Figure 1:
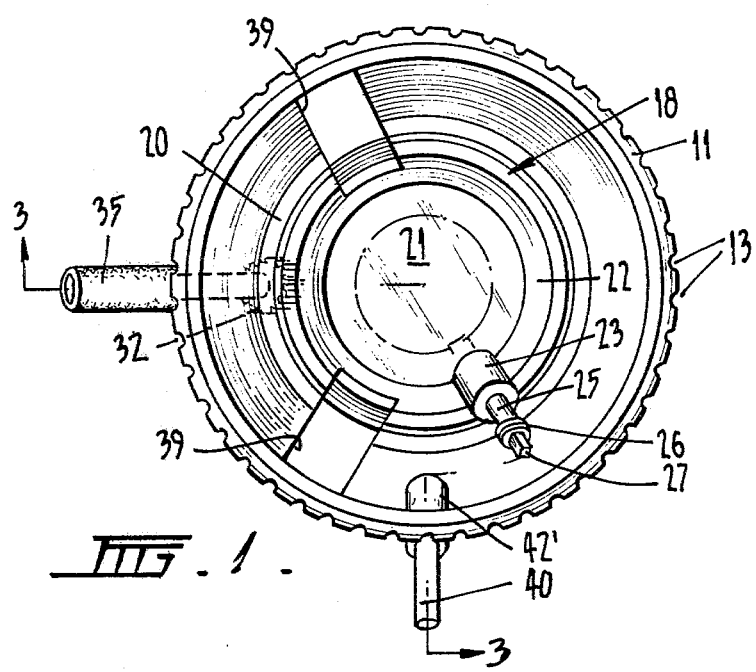

United States Patent [19]

Crock et al.

[11] 4,205,682
[45] Jun. 3, 1980

[54] CONTACT LENS CORNEAL CUTTER

[75] Inventors: Gerard W. Crock, Kew; Ljubomir Pericic, Alphington, both of Australia

[73] Assignee: The University of Melbourne, East Melbourne, Australia

[21] Appl. No.: 834,660

[22] Filed: Sep. 19, 1977

[30] Foreign Application Priority Data

Sep. 17, 1976 [AU] Australia ............................ PC7403

[51] Int. Cl.² ............................................ A61B 17/32
[52] U.S. Cl. .................................... 128/305; 128/749; 30/276; 30/293
[58] Field of Search ............... 128/2 B, 305, 310, 330, 128/749, 751, 755, 305, 330; 30/276, 293, 310; 408/146, 54, 89; 3/13

[56] References Cited

U.S. PATENT DOCUMENTS

| | | | |
|---|---|---|---|
| 2,249,906 | 7/1941 | Longovia | 128/305 |
| 2,486,737 | 8/1949 | Jayle | 128/305 |
| 3,074,407 | 1/1963 | Moon et al. | 3/13 X |

OTHER PUBLICATIONS

American Journal of Ophthalmology, "A New Corneal Trephinc", D. M. Lieberman, M.D., May, 1976, vol. 81, No. 5.
American College Dictionary, p. 997.

*Primary Examiner*—Robert W. Michell
*Assistant Examiner*—J. L. Krutor
*Attorney, Agent, or Firm*—Cushman, Darby & Cushman

[57] ABSTRACT

A cutter to remove corneas from eyes which includes a body adapted to be placed and held on an eye and which has a rotatable carriage including a contact lens which rests against the surface of the cornea to restrict movement thereof and which has associated therewith a knife, the depth of cut of which is adjustable so that on a combination of rotation of the carriage and adjustment of depth of cut the cornea can be removed, the removed cornea having a truncated conical outer surface. The specification also describes a surgical method of removing and replacing corneas in eyes.

17 Claims, 6 Drawing Figures

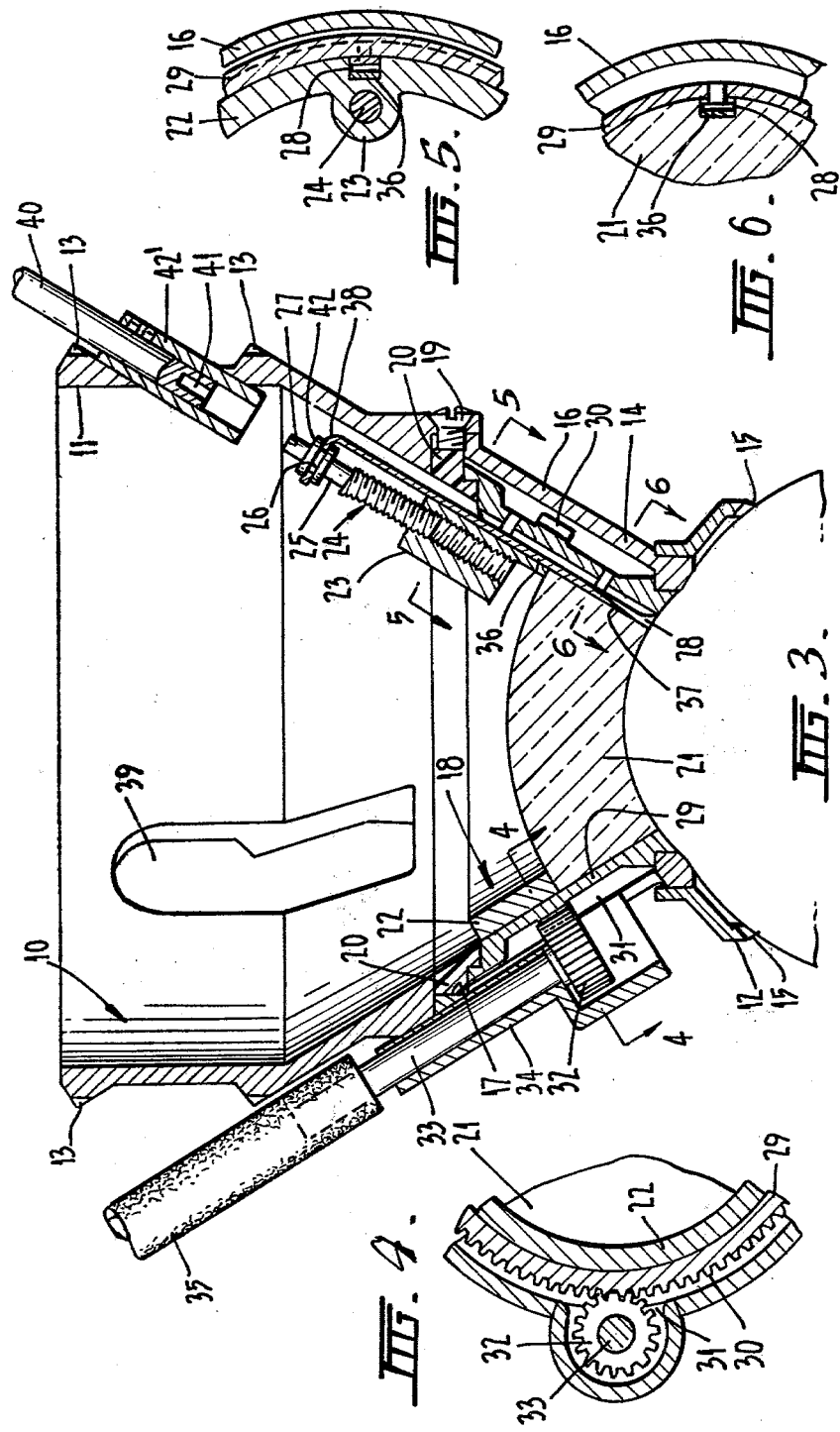

CONTACT LENS CORNEAL CUTTER

This invention relates to an improved corneal cutter.

Conventionally, when corneal transplants have had to be made, both the donor and the recipient have been operated on with a trephine which was in the form of a parallel sided punch and which was designed to remove the cornea from a cadaver so that the healthy cornea could be located in the eye of the person having an unhealthy cornea which was also removed by the trephine. The donor button was sewn into the recipient. The match was sufficient, hopefully, to enable the implant to take and for the recipient's sight to improve.

Such operations had difficulties in that they had to be done visually, without the full advantages of an operating microscope. Because of this the operating surgeon could not readily ascertain the actual location of the trephine and thus the area of the eye removed could be very inaccurate.

Recently a new form of trephine has been developed, apparently by David M. Lieberman M.D. of the Methodist Hospital, Brooklyn, New York, N.Y. and this device was described in the American Journal of Ophthalmology of May 1976, Volume 81 No. 5. This device, whilst an improvement on the conventional parallel sided trephine, still had disadvantages. This device included an inner ring which was adapted to rest against the eye, a frame attached to the inner ring and adapted to be held by a user to retain the inner ring in position and a body which carried a blade and which was adapted to be located relative to the frame and the inner ring. The body had associated therewith means by which the blade could be lowered towards the cornea and also had associated therewith means whereby the radial location of the blade relative to the inner ring could be varied.

This device necessitates the use of a pressure of 10-15 mm Hg which is considered, by some ophthalmologists, to be rather dangerous, causes a problem in visibility to the user and is rather difficult to operate as the body, which is rotated is relatively large and thus liable to disturbance.

An object of the present invention is to provide an improved corneal cutter which does not suffer from the major disadvantages of the previously known devices.

The corneal cutter includes a body in the form of a cup having a lower end adapted to rest against the surface of the eye and an enlarged upper end adapted to be held by the non-dominant hand of the user and a rotatable carriage located in and restrained by the body, the carriage having a knife carrier thereon, means to move a knife located in the carrier downwardly to extend beyond the carriage and a lens in the lower end of the carriage which is adapted to rest against the surface of the cornea to limit movement of the cornea relative thereto.

In a specific feature of the invention, the carriage is provided with a rack about its periphery and associated with the body there is a member carrying at its lower end a pinion which engages with the rack, the pinion having a drive shaft which extends upwardly along the outer surface of the body and which may have a flexible extension adapted to be manipulable by the user's dominant hand with minimal disturbance of the location of the body.

In a still further aspect, the carriage includes an elongated slot which is adapted to receive a blade, a member having a micrometer thread being located adjacent the slot and having a recess near its upper end, which recess is adapted to receive an inturned portion of the blade so that longitudinal movement of the blade is controlled by the position of the micrometer thread.

In another aspect, the member carrying the micrometer thread is inclined at an angle to the upper part of the body and at least one aperture is provided in the body to enable access to the head of this member to enable rotation thereof and thus the subsequent movement of the knife relative to the lens in the carriage.

In a still further aspect, the lens is relieved at one point thereof to enable the knife to pass through the lens in such a way that a user can see the location of the outside of the cut formed by the knife in the cornea.

Figure 2:
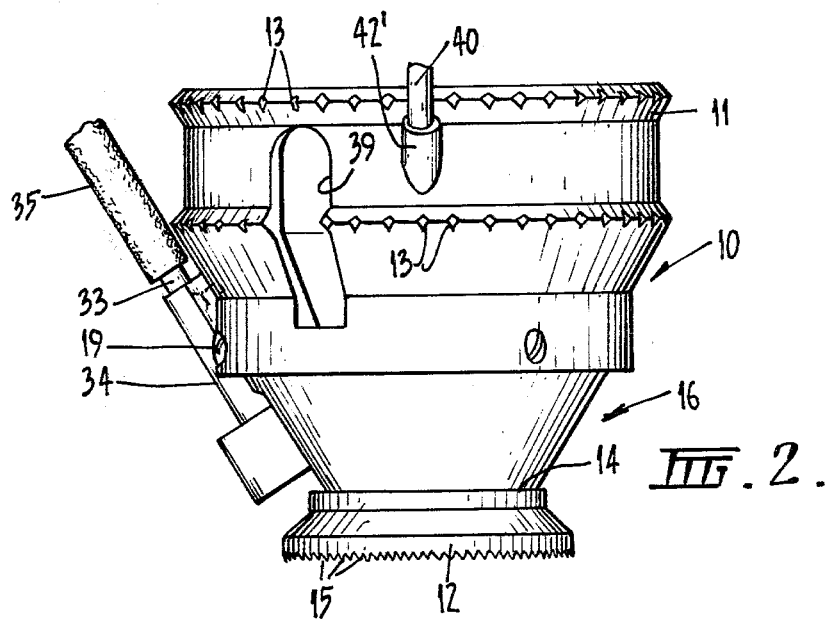

In order that the cutter can be more readily understood, one embodiment of a corneal cutter made in accordance with the invention will be described in relation to the accompanying drawings in which:

FIG. 1 is a plan view of the cutter of the invention;
FIG. 2 is a side elevation of the cutter;
FIG. 3 is a section along line 3—3 of FIG. 1 and shows the carriage driving member, the micrometer threaded member and the micrometer adjustment member;
FIG. 4 is a section along line 4—4 of FIG. 3;
FIG. 5 is a section along line 5—5 of FIG. 3: and
FIG. 6 is a section along line 6—6 of FIG. 3.

In the illustrated embodiment the cutter has a body 10 which is basically in the form of a cup which, at its upper end 11, may be some 3 cm in diameter and which, at its lower end 12, its some 2 cm in diameter and which has adjacent its lower end 12 a smaller diameter portion which may be approximately 1.5 cm. This body, which is preferably of stainless steel or some other metal which can be autoclaved without damage, and preferably having a relatively small co-efficient of expansion, may be formed at its upper end to have ribs, serations, roughenings or other uneven areas 13 to enable easy handling and retention by the non-dominant hand of the user. At the lower edge of this ribbed or otherwise treated surface the body tapers in conically to the minimum diameter portion 14. After reaching its minimum diameter portion, the body flares outwardly and at its lower edge may be provided with serations 15 or the like which are adapted to aid the retention of the body on the eye.

The body may be made of a single piece of metal or may be a composite of various parts which can be held together mechanically, as by screws, or physically, as by an autoclavable adhesive such as a silicone rubber.

The lower end portion 12 may desirably be separate from the remainder of the body so that this may be one of a number of interchangeable portions which are of different diameter. In this way the cutter is readily adaptable to eyes of varying sizes.

As illustrated, the body is formed of three portions, the upper one of which carries the serations 13, the central portion 16 is in the form of a truncated cone and the lower portion 12 is the removeable portion having serations 15. Between the upper and central portions there is formed a recess 17 in which there is located a bearing 20 made of 'Teflon' (Registered Trade Mark). This bearing 20 is located after the carriage 18, to be described later, is positioned in the central portion 16 and before the upper portion is positioned. After the members are assembled they are held together by screws 19.

Alternatively the carriage 18 and the body may be in a metal to metal contact arrangement but we have found this not to be completely satisfactory.

The carriage 18, when located within the central portion 16 of the body is adapted to be rotated relative thereto. The rotation should be with a minimum of disturbance and this is why we provide the bearing 20. If no bearing is used the body and the carriage should be of different metals or different alloys of the same metal to enable an effective bearing which provides smooth movement to be formed.

At its lower end the carriage has a lens 21 which is preferably of quartz as it needs to accept high temperatures with a low co-efficient of expansion and this lens is bonded to the carriage by means of an adhesive and, again, preferably a silicone adhesive. This bonding is most satisfactory as the co-efficient of expansion of stainless steel and quartz are substantially different and such a bond can absorb this difference.

Located in the carriage body 29 and above the lens 21 there is a ring 22 which aids the retention of the lens and has located therein a threaded sleeve 23.

Located in the sleeve 23 there is a correspondingly threaded blade carrier and adjustment member 24. The threads on the sleeve 23 and the threaded member 24 are preferably micrometer threads.

The threaded member 24 has adjacent its upper end an extension 25 which has a peripheral groove 26 and above this extension a key receiving portion 27.

Located within the carrier outwardly of the member 24 and between the member and the body there is a groove 28 which passes to the exterior of the cutter. The actual point at which the blade passes to the exterior can be at the junction of the carriage body 29 and the lens but, preferably, and as illustrated, is within the periphery of the lens. The reason for this will be explained hereinafter.

On the exterior of the carriage body 29 part way down the conical portion there is formed a peripheral rack 30 or fixed ring gear. The body has an aperture 31 which opens on to this rack and adjacent the aperture there is located a pinion member 32 which meshes with the rack and which has a shaft 33 which extends outwardly and upwardly through a journal 34 which is itself attached to the body member. The arrangement is such that when the shaft 33 is rotated this causes an equivalent rotation of the pinion 34 and the positive rotation of the carriage 18. The actual degree of rotation of the carrier is not greatly important as the speed of rotation of an instrument of this type need not be high. Evenness of rotation is, however, important. We prefer that the shaft extends beyond the upper surface of the journal 34 and has fitted thereover an extension 35 which may be a tube of silicone rubber and which, in turn extends above the body so there is no likelihood of confusion between the non-dominant hand holding the body and the dominant hand rotating the shaft.

The blade which is preferably made from a high quality stainless steel is of such a size as to be received in the slot 28 which is located behind the micrometer threaded member 24 and is, at its lower end 37, preferably sharpened to a point and has a side cutting surface. The blade, at its upper end 38, is formed with an inwardly directed portion and the location of the head of the micrometer adjustment member is such that the blade cannot pass from above or below this member without distortion. In practice, the upper end 38 of the blade is distorted until its inturned portion can enter the recess 26 in the head of the micrometer adjustment member and in this way the position of the blade relative to its egress through the lens 21 can be controlled.

Formed in the body there is at least one cutout portion 39 which is arranged to enable, when it is oriented adjacent the threaded member 24, a blade 36 to be passed behind the threaded member and into the groove 28. It can readily be seen, from FIG. 3, that if such a cutout was not provided the blade could not be located in the slot.

Located in the wall of the body there is a sleeve 42' which, when located above the threaded member 24 is co-axial therewith. The sleeve 39 is adapted to receive a key 40 which is formed at its lower end 41 to co-operate with the key receiving portion 27 of the threaded member 24, thus, when the threaded member 24 and the sleeve are co-axial the key 40 can be moved downwardly to engage the threaded member and, on rotation, can cause the threaded member to move relative to its sleeve 23. If a blade is located this movement is reflected on the blade and it can be caused to extend a further or less distance through its slot and thus beyond the groove 28 where it leaves the lens 21. When the carriage is to be rotated, the key 40 must be moved outwardly and a stop or the like can be provided.

In use the cutter is sterilized as by autoclaving and a blade 36 which may be sterilized by autoclaving, by gas or radiation is introduced into one of the cutouts 39 in the side of the body and through this into the groove 28 formed behind the micrometer threaded member 24. The blade is moved down the groove until its inturned upper end 38 strikes the top of the annular extension 42 which forms the upper side of the groove 26 at which time it can be distorted, passed over the extension 42 and enter the peripheral groove 26 of the micrometer adjustment member. At this time, if necessary, the micrometer adjustment member can be manipulated until the blade does not extend beyond the lens 21. This is the condition illustrated in FIG. 3.

The cutter, which has been maintained sterile, is then brought into contact with the doner or recipient's eye with the serations 15 on the lower end of the body in contact with the eye to prevent movement thereof. The surgeon, using an operating microscope can look through the lens 21 and see whether the cutter is centrally located. If so the micrometer can be brought into alignment with the sleeve 42', the key 40 is moved downwardly until the formed lower end 41 co-operates with the end 27 of the threaded member 24. The key can be rotated until the knife 36 can be seen to contact the cornea. At this time manipulation of the silicone rubber tube 35 will cause rotation of the carriage 18 and the knife will commence to cut into the cornea. We have found that as the cornea is restrained by the lens 21 it tends not to move, as has previously been the case, and the cut is relatively the same regardless of the direction of fibres in or adjacent the cornea.

At all times, because of the location of the blade 36, the user can ascertain the position of the cut being made and thus can ensure that the cutter has not, accidently, been moved from its original position. When a cut has been made completely around the cornea the key 40 can be fitted on to the threaded member 24 and, on rotation, will increase the depth of cut, by say of the order of 0.3 mm. The operation can be continued until the user can either visually ascertain that the cornea has been cut to the required depth which may be through the cornea or which may be of a depth that he believes the use of an alternative instrument such as a vibrating knife can complete the cut.

It will be seen that as the knife of the present invention is located at an axis to the angle of the cutter, and thus at an angle to the cornea, that the portion removed will be wedge shaped inwardly rather than parallel sided. When this cornea is to be fitted to a recipient, who also has his cornea removed by the same process, then the two tend to match extremely well and a competent ophthalmic surgeon can ensure an almost perfect match. At the same time there is little likelihood that the cornea will be displaced downwardly more than would be desirable because of the wedge shapes of the two components.

The invention also relates to a method of ophthalmic surgery using the corneal cutter of the invention.

The method includes the steps of locating the cutter over a cornea, either with or without some irrigating fluid between the cornea and the lens and by examination of the eye a surgeon can decide whether or not the lower end 12 is of the correct size for the particular eye and, if necessary, this can be replaced. The surgeon then examines the eye through an operating microscope and, by looking through the lens 21 can ascertain if the instrument is correctly located. When it is located the key 40 is moved over the formed end 27 of the threaded member 24 and the key is rotated until the end 37 of the knife penetrates the cornea and rotation is then continued through a predetermined angle at which time the key is withdrawn outwardly so as not to foul the knife carrier and the flexible extension 35 associated with the pinion 32 is rotated until the first, circular, cut is made. The key is then re-engaged and rotated through a predetermined angle, is disengaged, and the carriage is, again, rotated. These steps are repeated until the required depth of cut has been achieved and the cornea is ready for removal, either directly or after separation as with an oscillating or standard knife. Preliminary stitches can then, if required, be put into the cornea and it can be removed directly on to a supporting frame minimizing handling of the cornea. The cornea on its frame can be transported to the recipient of the cornea.

In a hospital, under sterile conditions, the procedure is repeated with the cornea of the recipient's eye being removed. Because the donor's cornea and the recipient's cornea are both removed with what are effectively identical instruments, the portion removed from the recipient's eye is wedge shaped and is effectively identical to that from the donor's eye as in each case the cornea was restrained from movement whilst being removed. To complete the operation it is only necessary to stitch the cornea into the recipient's eye.

We claim:

1. A corneal cutter including a body in the form of a cup having a lower end adapted to rest against the surface of the eye and an enlarged open upper end to view the eye adapted to be held by the non-dominant hand of the user and a carriage rotatable about an axis passing through the plane of the upper and lower end of the cup located in and restrained by the cutter body, a solid lens in the lower end of the carriage which is adapted to rest against the surface of the cornea to limit movement of the cornea relative thereto, a knife supported on the carriage, and means for moving the knife downwardly relative to the carriage and the lens so as to extend beyond the carriage and the lens.

2. A corneal cutter as claimed in claim 1 wherein the carriage has a ring shaped rack about its periphery and wherein a pinion, fixed relative to the body engages the rack, the pinion being associated with a shaft, rotation of the shaft causing rotation of the carriage.

3. A corneal cutter as claimed in claim 2 wherein the shaft has a flexible extension thereon.

4. A corneal cutter as claimed in claim 1 wherein the means for supporting the knife includes a micrometer screw member engaged with a threaded sleeve on the inside of the carriage, the screw member having means whereby a knife can be engaged therewith, rotation of the member controlling the movement of the blade relative to the carriage.

5. A corneal cutter as claimed in claim 4 wherein the screw member has an annular recess adjacent its upper end and the knife has an inturned portion at its upper end, the knife being deformed to permit the inturned portion to enter the recess.

6. A corneal cutter as claimed in claim 4 wherein the carriage has an elongated slot into which the blade passes and through which it extends when cutting is required.

7. A corneal cutter as claimed in claim 6 wherein at least part of the slot is in the lens.

8. A corneal cutter as claimed in claim 7 wherein the slot is at an angle to the axis of the lens so that when the knife is extended beyond the carriage the tip of the knife can be seen through the lens.

9. A corneal cutter as claimed in claim 4 wherein there is a sleeve in the body which sleeve, when in alignment with the screw member is co-axial therewith, the sleeve being adapted to receive a key so formed as to be capable of engagement with the head of the screw member and, when engaged, able to cause rotation thereof.

10. A corneal cutter as claimed in claim 9 wherein the sleeve and/or the key has means whereby when the key is moved outwardly so as not to obstruct rotation of the carriage when contact with the screw member is not required the key is retained in this position.

11. A corneal cutter as claimed in claim 10 wherein the key has a flexible extension thereon.

12. A corneal cutter as claimed in claim 1 wherein the body has at least one aperture therein to enable a knife to be inserted into the means for supporting the knife.

13. A corneal cutter as claimed in claim 1 wherein the outer surface of the body is formed to provide a good hand grip.

14. A corneal cutter as claimed in claim 1 wherein the lower end is so formed as to grip the surface of the eye.

15. A corneal cutter as claimed in claim 14 wherein the lower end of the body is removeable.

16. A method of ophthalmic surgery comprising the steps of locating a corneal cutter as claimed in claim 1 on a donor's eye in a manner such that the lower end of the body and the lens engage the cornea, extending the knife to contact the periphery of the cornea, rotating the carriage, extending the knife and again rotating the carriage, repeating these steps until the cut is of the required depth, removing the donor cornea in a wedge shape, repeating the steps on the recipient's eye, placing the donor's cornea in the recipient's eye and stitching the cornea into position.

17. A method as claimed in claim 16 wherein initial stitches are placed into the donor's cornea on removal the stitches permitting the cornea to be moved or located on a transport frame with minimal handling.

* * * * *